United States Patent
Halvorson et al.

(10) Patent No.: US 8,745,298 B2
(45) Date of Patent: Jun. 3, 2014

(54) INTEROPERABILITY ENHANCEMENT THAT SUPPORTS CONNECTIVITY OF APPLICATIONS ON A MEDICAL DEVICE

(75) Inventors: Christopher R. Halvorson, Carmel, IN (US); James R. Long, Fishers, IN (US); Ryan S. McKinney, Brownsburg, IN (US); Adam R. Scroggin, Noblesville, IN (US); Morris J. Young, Noblesville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 120 days.

(21) Appl. No.: 13/279,857

(22) Filed: Oct. 24, 2011

(65) Prior Publication Data

US 2013/0102853 A1 Apr. 25, 2013

(51) Int. Cl.
*G06F 13/00* (2006.01)
(52) U.S. Cl.
USPC ............... 710/305; 710/72; 604/65; 604/66; 604/67; 604/300
(58) Field of Classification Search
USPC ................... 604/65, 66, 67; 710/305, 72
See application file for complete search history.

(56) References Cited

U.S. PATENT DOCUMENTS

| | | | | |
|---|---|---|---|---|
| 7,481,763 | B2 * | 1/2009 | Hassler et al. | 600/37 |
| 8,103,241 | B2 * | 1/2012 | Young et al. | 455/404.1 |
| 8,280,849 | B2 * | 10/2012 | Baker et al. | 707/617 |
| 8,551,070 | B2 * | 10/2013 | Miller et al. | 604/500 |
| 8,612,163 | B2 * | 12/2013 | Hayter et al. | 702/23 |
| 2004/0260233 | A1 * | 12/2004 | Garibotto et al. | 604/66 |
| 2008/0055039 | A1 * | 3/2008 | Eberhart et al. | 340/5.2 |
| 2010/0169119 | A1 * | 7/2010 | Hussain | 705/3 |

OTHER PUBLICATIONS

"Getting Started, CareLink Personal Therapy Management Software for Diabetes," Brochure, 2007, 20 pp., Medtronic MiniMed, Inc.*
Part 20601: Application Profile—Optimized Exchange Protocol, IEEE Std 11073-20601 Sep. 26, 2008.
Part 10417: Device Specialization—Glucose Meter, IEEE Std 11073-10417, May 8, 2009.
Continua Design Guidelines 2010, Oct. 1, 2010.
HealthLink PC Webpage, www.lampreynetworks.com, Oct. 24, 2011.
Piniewski et al., "Empowering Healthcare Patients With Smart Technology", Computer, IEEE Service Center, Los Alamitos, vol. 42, No. 7 (2010).
ISO/IEEE 11073 Personal Health Data (PHD) Standards, (2011).
ISO/IEEE 11073 (2011) XP055049333.

* cited by examiner

*Primary Examiner* — Tammara Peyton
(74) *Attorney, Agent, or Firm* — Harness, Dickey

(57) ABSTRACT

A diabetes management system is provided that supports connectivity of applications residing on a medical device. The diabetes management system includes a medical device that performs a diabetes care function in relation to a patient and a diabetes care management device in data communication with the medical device. The diabetes care management device is comprised generally of a connection management module and at least one application separate from the connection management module. The connection management module is configured to receive an associate request from the medical device and operable to establish a data connection with the medical device in accordance with IEEE standard 11073, such that the applications interacts with the connection management module to communicate via the data connection with the medical device.

16 Claims, 9 Drawing Sheets

INTEROPERABILITY ENHANCEMENT THAT SUPPORTS CONNECTIVITY OF APPLICATIONS ON A MEDICAL DEVICE

FIELD

The present disclosure relates generally to an interoperability enhancement that supports multiple applications residing on a medical device and, more particularly, enables connectivity of the applications in compliance with Continua design guidelines.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex as the level of blood glucose entering the bloodstream is dynamic. Variation of insulin in the bloodstream that controls the transport of glucose out of the bloodstream also complicates diabetes management. Blood glucose levels are sensitive to diet and exercise, but also can be affected by sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is often highly intrusive because of the need to consistently obtain reliable diagnostic information, follow prescribed therapy, and manage lifestyle on a daily basis. Daily diagnostic information, such as blood glucose concentration, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data that are acquired from medical devices, personal healthcare devices, patient recorded information, healthcare professional tests results, prescribed medications and recorded information. Clinicians generally treat diabetic patients according to published therapeutic guidelines such as, for example, Joslin Diabetes Center & Joslin Clinic, *Clinical Guideline for Pharmacological Management of Type 2 Diabetes* (2007) and Joslin Diabetes Center & Joslin Clinic, *Clinical Guideline for Adults with Diabetes* (2008). The guidelines may specify a desired biomarker value, e.g., a fasting blood glucose value of less than 100 mg/dl, or the clinician can specify a desired biomarker value based on the clinician's training and experience in treating patients with diabetes. However, such guidelines do not specify biomarker collection procedures for parameter adjustments to support specific therapies used in optimizing a diabetic patient's therapy. Subsequently, diabetic patients often must measure their glucose levels with little structure for collection and with little regard to lifestyle factors. Such unstructured collection of glucose levels can result in some biomarker measurements lacking interpretative context, thereby reducing the value of such measurements to clinicians and other health care providers. Thus, there is a need to provide structured collection procedures for diagnostic or therapy support of a patient with diabetes or other chronic diseases.

Patients with diabetes and their healthcare professionals interact with a variety of medical devices and systems to help manage the disease. For each of these differing types of medical devices, there is a need to aggregate, manipulate, manage, present, and communicate diagnostic data and prescriptive data from multiple data sources in an efficient manner to improve the care and health of a person with diabetes, so the person with diabetes can lead a full life and reduce the risk of complications from diabetes. There is also a need to aggregate, manipulate, manage, present, and communicate such diagnostic data and prescriptive data amongst the different types of medical devices using a standard communication protocol.

Continua Health Alliance is a trade association working toward establishing systems and standards for interoperable medical devices. Design guidelines put forth by Continua leverage various IEEE standards including IEEE 11073 which pertains to the interoperability of personal health devices. In the Continua paradigm, devices take on the lead role in establishing a data connection with other devices. As such, health care management systems operated by healthcare providers must adapt from an initiator role to a "listening" role. Therefore, it is desirable to provide an interoperability enhancement that supports connectivity of devices in compliance with Continua design guidelines while continuing to support legacy devices. Additionally, the interoperability enhancement should support multiple applications residing on a single device, including contention resolution amongst applications accessing a given data connection.

The background description provided herein is for the purpose of generally presenting the context of the disclosure.

SUMMARY

A diabetes management system is provided that supports connectivity of applications residing on a medical device. The diabetes management system includes a medical device that performs a diabetes care function in relation to a patient and a diabetes care management device in data communication with the medical device. The diabetes care management device is comprised generally of a connection management module configured to receive an associate request from the medical device and operable to establish a data connection with the medical device in accordance with IEEE standard 11073; as well as at least one application separate from the connection management module, such that the application interacts with the connection management module to communicate via the data connection with the medical device.

In one aspect of this disclosure, a listing of devices interoperable with the diabetes care management device is made accessible to the connection management module. Upon receipt of an associate request, the connection management module queries the listing of devices and establishes the data connection when the associate request is received from a medical device on the listing of devices. On the other hand, the connection management module operates to disassociate from the medical device when the medical device is not on the listing of devices.

In an alternative configuration, the listing of devices interoperable with the diabetes care management device is made accessible to the first application. The first application queries the listing of devices and establishes the data connection when the associate request is received from a medical device on the listing of devices.

In another aspect of this disclosure, the connection management module receives a registration request from the first application for the data connection with the medical device and registers the data connection for use by the first application. The connection management module then receives messages over the data connection from the medical device and routes the messages to the first application.

The connection management module is further configured to receive data over the data connection from the medical device and store the data for subsequent access by a client application in a transient data store accessible to the connection management module.

In yet another aspect of this disclosure, the connection management module establishes an inter-process communication (IPC) channel for communication with the first application. The first application operates over the IPC channel to acquire a reference to a remotable object from the connection management module and instantiates the remotable object, where the remotable object exposes methods which allow the first application to communicate with the connection management module. The connection management module may communicate with the first application in accordance with the .NET framework.

In another aspect of this disclosure, the diabetes management system also supports contention resolution amongst two to more applications residing on a diabetes care management device. In addition to the connection management module, the diabetes care management device includes a first application separate from the connection management module; a second application separate from the connection management module and residing on the diabetes care management device; and a contention manager configured to receive a request to access the data connection from both the first and second application and operable to grant access to one of the first application or the second application in accordance with an access rule.

Further areas of applicability of the present disclosure will become apparent from the detailed description provided hereinafter. It should be understood that the detailed description and specific examples are intended for purposes of illustration only and are not intended to limit the scope of the disclosure.

Figure 2:
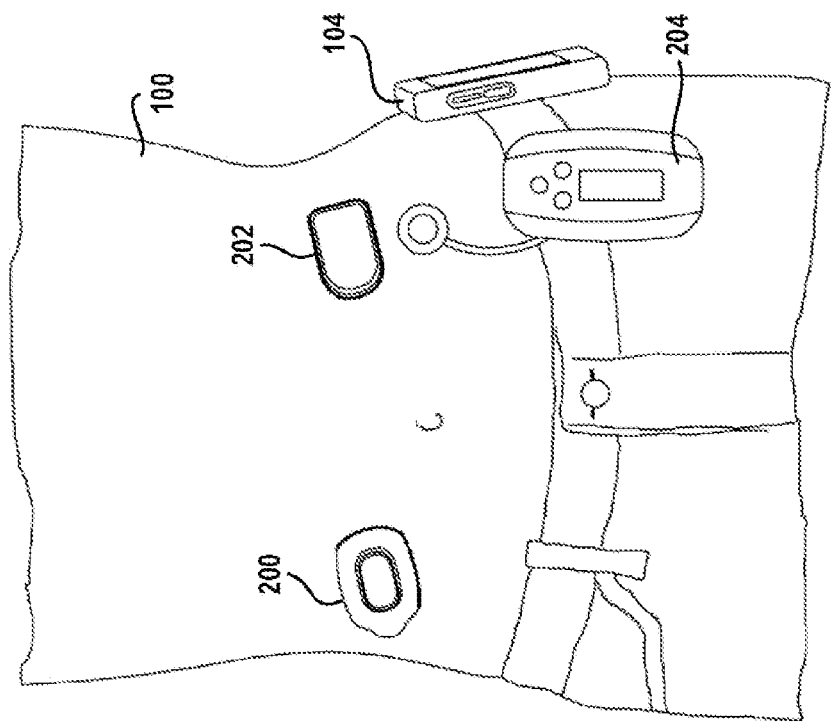
FIG. 2 is a diagram showing the patient with a continuous glucose monitor (CGM), an ambulatory durable insulin infusion pump, an ambulatory non-durable insulin infusion pump, and a diabetes manger.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Figure 1:
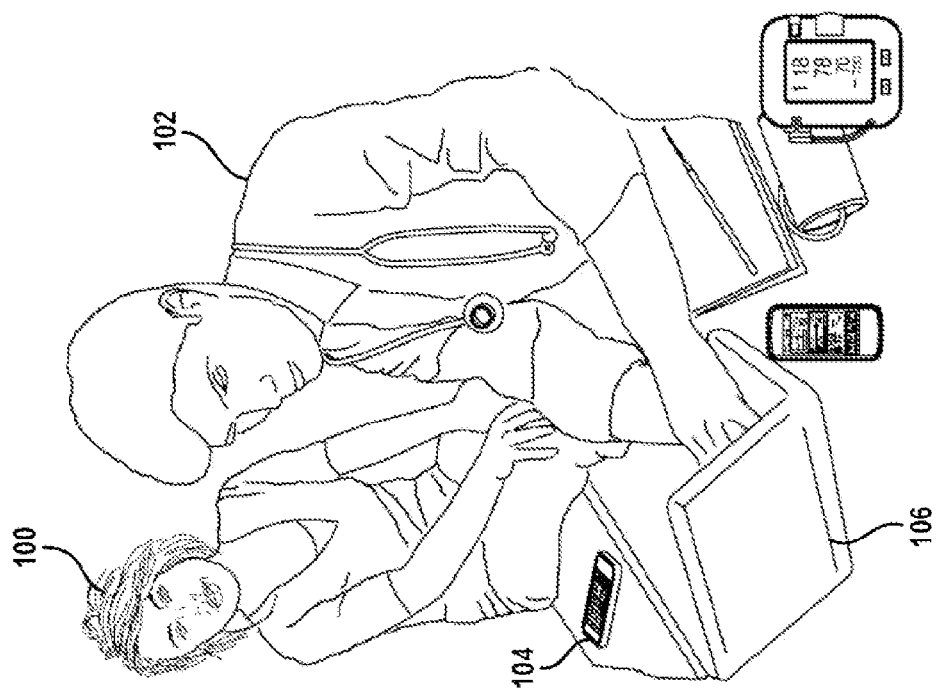
FIG. 1 is a diagram showing a patient and a treating clinician.

With reference to FIG. 1, a person 100 with diabetes and a healthcare professional 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician. While reference is made throughout this disclosure to diabetes care, it is readily understood that the concepts disclosed herein can be applied to other types of chronic diseases.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. The patient data can be recorded manually or electronically using one of various types of diabetes care management devices, such a handheld diabetes management device 104, diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

In an exemplary treatment scenario, the patient 100 may use various medical devices as shown in FIG. 2. The handheld diabetes manager 104 performs various tasks including measuring and recording blood glucose levels, determining an amount of insulin to be administered to the patient 100 via the insulin pump 202 or 204, receiving patient data via a user interface, archiving the patient data, etc. Thus, the diabetes manager 104 is configured to serve as a system hub and communicates with the devices which comprise the diabetes management system.

For instance, the diabetes manager 104 can receive blood glucose readings from one or more sources (e.g., from the CGM 200). The CGM 200 continuously measures the blood glucose level of the patient 100. The CGM 200 periodically communicates the blood glucose level to the diabetes manager 104. The diabetes manager 104 and the CGM 200 communicate wirelessly using, for example, a proprietary Gazell wireless protocol developed by Nordic Semiconductor, Inc.

The diabetes manager 104 may include a blood glucose meter (BGM) and a port that communicates with the BGM (not shown). The port can receive a blood glucose measurement strip 306. The patient 100 deposits a sample of blood or other bodily fluid on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100. To facilitate collection of blood glucose measures, the diabetes manager 104 may executes one or more structured collection procedures as further described below.

Additionally, the diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information. The insulin pump 202 or 204 can also communicate data to the diabetes manager 104. The data can include amounts of insulin delivered to the patient 100, corresponding times of delivery, and pump status.

Communication between the devices in the diabetes management system can be performed using wireless interfaces (e.g., Bluetooth) and/or wireline interfaces (e.g., USB). Likewise, the devices may employ different types of communication protocols, including protocols compliant with the IEEE 11073 standard and extended using design guidelines provided by Continua® Health Alliance. The diabetes management system may also include other types of medical devices used in treatment of diabetes including but not limited to a blood pressure meter, a weight scale, a pedometer, a fingertip pulse oximeter, a thermometer, etc.

Figure 3:
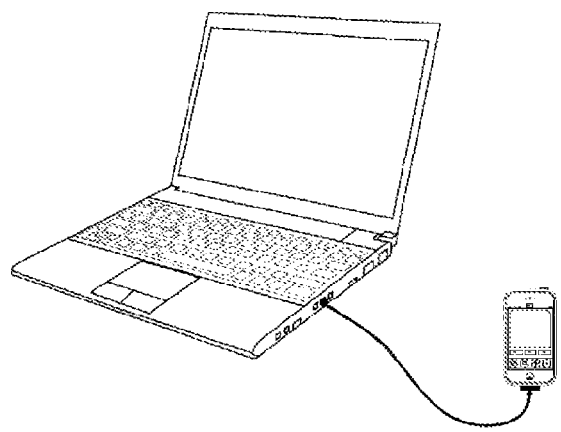
FIG. 3 is a diagram showing a diabetes manager coupled to a physician's desktop PC.

One or more of these patient devices may also interface with computing devices associated with a healthcare provider. With reference to FIG. 3, the diabetes manager 104 is coupled to a desktop personal computer 302. The desktop PC is equipped with diabetes management software application to assist the healthcare provider with treatment of the patient. For instance, the software application may enable the healthcare provide to retrieve and analyze personal health data from the diabetes manager 104. The software application may further enable the healthcare provider to configure operating parameters on the diabetes manager 104. Accu-Chek 360® Diabetes Management System is an example of a commercially available diabetes management software product although other products having similar functionality also fall within the scope of this disclosure.

Figure 4:
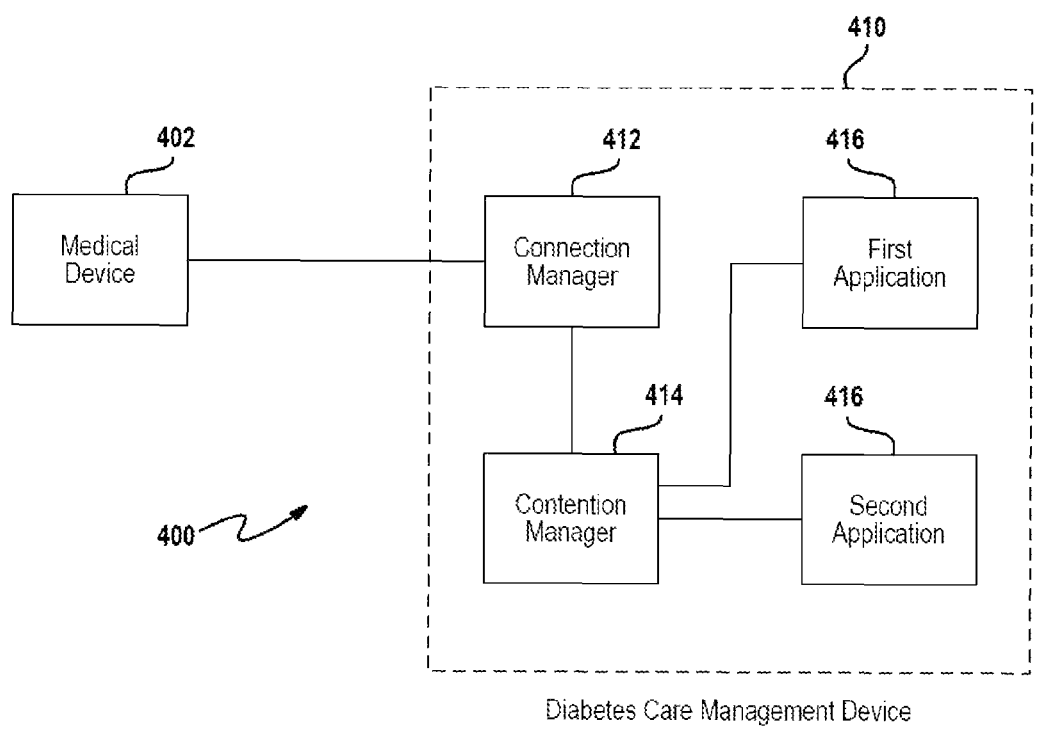
FIG. 4 is a block diagram showing an exemplary diabetes management system used by patients and clinicians to manage diabetes.

FIG. 4 illustrates an exemplary communication model for the diabetes management system. In general, the diabetes management system 400 is comprised of a diabetes care management device 410 and at least one medical device 402, where the medical device 402 performs a diabetes care function in relation to a patient and stores data resulting from the function. The diabetes care management device 410 further includes a connection manager 412, a contention manager 414 and one or more client applications 416. In one exemplary scenario, an insulin pump 202 is a medical device 402 communicating with a diabetes care management device 410, such as the diabetes manager 104. In another exemplary scenario, the diabetes manager 104 is the medical device 402 communicating with a physician's PC acting as the diabetes care management device 410. It is to be understood that the diabetes care management device 410 is comprised of other components but that the components relevant to this disclosure are discussed in relation to FIG. 4.

In an exemplary embodiment, communication between the devices occurs in accordance with IEEE standard 11073. The communication model employs the concept of "managers" and "agents". Agents are generally smaller personal health devices that lack processing power; whereas, managers are more powerful computing devices such as a smart phone or desktop computer. To communicate, an agent initiates an association between itself and a manager. The agent issues an association request and the manager responds with an acceptance of the association request. In this way, the agent and manager form an association and enter into an operating state. In the context of FIG. 4, the medical device 402 acts as an "agent" and the diabetes care management device 410 acts as a "manager".

To support connectivity amongst an agent and two or more client applications residing on a manager, the communication model has been extended. Specifically, managers are equipped with a connection manager 412 that manages the data connections between an agent and a manager. In operation, the connection manager 412 receives associate requests from a medical device 402 and operates to establish connections with the medical device 402 in accordance with IEEE standard 11073. The connections may include control connections or both control and data connections. By serving as an intermediary, the connection manager 412 allows clients to delay connection and thereby maintain the current user-driven flow. The connection manager 412 is preferably implemented as a computer program residing on the diabetes care management device 410 and executable by a processor residing on the device. It is noted that the connection manager 412 is separate and distinction from the client applications 416.

Two or more client applications may seek use of the connection to the medical device. For example, a first application may seek to retrieve patient data stored on the medical device while a second application may enable a health care provider to configure operating parameters on the medical device. To mitigate amongst requests to access the data connection by client applications, the connection manager 412 cooperatively operates with a contention manager 414. Upon receipt of a request to access the data connection, the contention manager 414 operates to grant or deny the access request to the requesting application in accordance with an access rule.

Contention resolution is preferably implemented in a centralized manner but may also be distributed and implemented by the client applications.

Figure 5A:
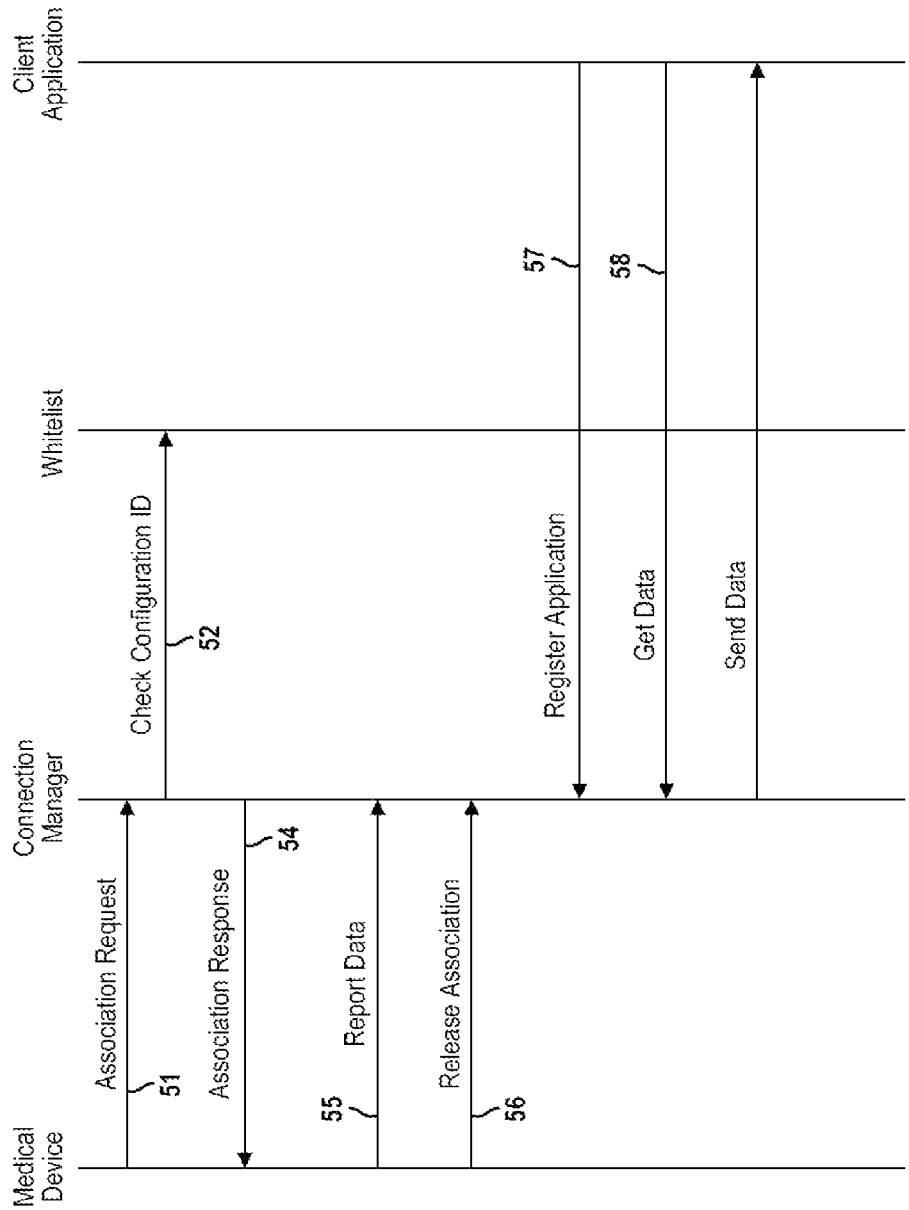
FIGS. 5A and 5B are sequence diagrams illustrating the operation of an exemplary connection manager.
Figure 5B:
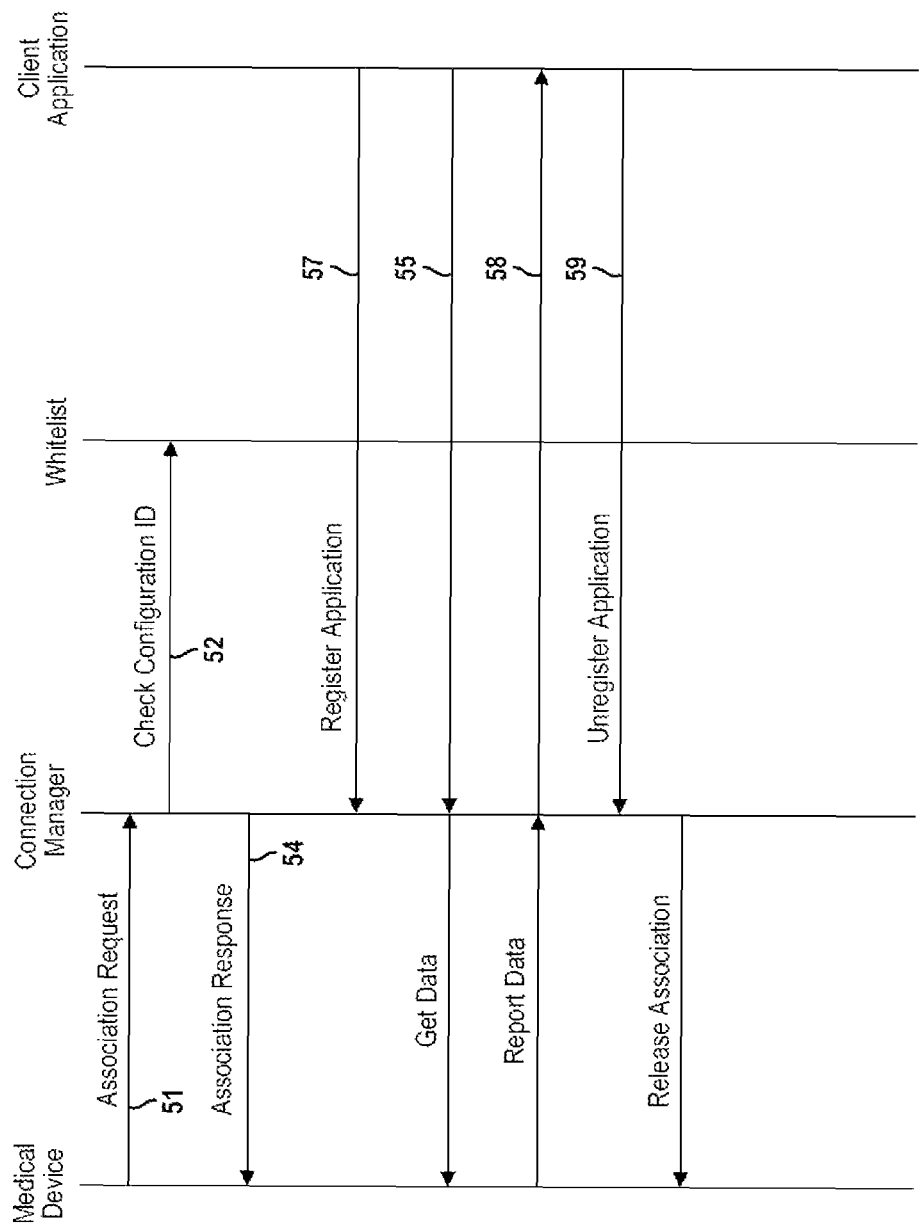

FIGS. 5A and 5B further illustrate the operation of the connection manager 412. The medical device 402 initiates the associate by sending an association request at 51 to the connection manager 412. The association request includes a configuration identifier for the medical device 402. In an exemplary implementation, the configuration identifier specifies the device type. For example, the device type may be a glucose meter, an insulin pump or a weight scale. The connection manager 412 will in turn query at 52 a listing of devices interoperable with the diabetes care management device (also referred to herein as a whitelist). When an associate request is received from a medical device having a type found in the listing, the connection manager 412 accepts the association request at 54 and forms an association with the medical device 402. On the other hand, when an associate request is received from a medical device having a type not found on the list, the connection manager 412 responds with a release association response to the medical device 402 and thereby disassociates from the medical device. The connection manager may also support an extended configuration for which the medical device type is not readily available. In this case, the connection manager would send an unknown configuration response to the medical device. Additionally, the connection manager may pass along the data sent in the configuration report to the client applications. The application would in turn determine whether to keep the connection open based on whether the data sent in a configuration report is supported or not by the diabetes care management device. Similar evaluation of the data sent in the configuration report could also performed by the connection manager. The connection is maintained when the data sent is supported but otherwise the connection can be discontinued.

In an alternative configuration, each client application has an associated whitelist. Rather than maintaining a single listing for the diabetes care management device, a listing is maintained for each client application. In this arrangement, upon registering with the connection manager, the registering client application will check its associated whitelist for the medical device. When the medical device is found on the listing, the registration of the application with the connection manager is completed. In another alternative configuration, a whitelist is not used. A connection is made between the management device and the associated medical device and data is exchanged. The data is then evaluated to determine whether the data will be used.

The medical device 402 may operate in different manners once an association has been made. For some types of devices, the medical device 402 reports data without any prompting to the diabetes care management device as shown in FIG. 5A. For instance, once a connection has been established, weight scales are typically configured to report patient weight data at 55 and then disassociate at 56 from the diabetes care management device. In these instances, the connection manager receives the reported patient data and stores the reported data in a transient data store accessible to the connection manager. At some later time, a client application will register at 57 with the connection manager and retrieve the patient date at 58 from the connection manager. In this way, the connection manager is configured to support these types of medical devices.

For other types of devices, the medical device interacts directly with a client application residing on the diabetes care device as shown in FIG. 5B. The client application initiates the interaction by registering at 57 with the connection manager 412. Once the client application is registered, the connection manager 412 supports pass through communication between the client application and the medical device. That is, the client application may query the medical device for patient data as indicated at 55 or the medical device may report patient data to the client application as indicated at 58. Upon completing its interactions with the medical device 402, the client application unregisters at 59 with the connection manager 412. The connection manager 412 may at that time release the association with the medical device 402 or maintain the association in the event another application registers against the medical device 402. In this way, the connection manager 412 operates in accordance with IEEE 11073.

In an exemplary embodiment, the diabetes care management device supports the .NET framework running on a Microsoft Windows operating system. In this environment, the connection manager 412 uses the .NET Remoting interface to communicate directly across the application domain boundary. For any .NET Remoting application, you must have a remotable object; a host application domain to listen for requests for that object; and a client application domain that makes requests for that object. To begin communication, a client application must open a connection to the host application's Remoting channel and request the remotable object. The remotable object exposes methods which allow the client and host application to communicate through normal object-oriented mechanisms. Once the remotable object has been acquired from the host application, any object that is serializable can be passed between the host and client. At this point, all communication is done through object interfaces, and the application code looks identical to normal, non-distributed applications. While reference is made to .NET Remoting, it is readily understood that other types of remote invocation methods may be employed for communicating between the connection manager and client applications To communicate, the connection manager 412 first establishes a channel for communicating with the client applications 416. In the exemplary embodiment, the connection manager 412 creates an IPC (Inter-Process Communication) channel for communication with client applications, referred to herein as IpcServerChannel. The IpcServerChannel allows client-initiated communication. The channel created by the connection manager 412 used a port name that must be unique, such as "Connectivity:RCM". Client applications must also register an IPC channel to handle messages coming from the connection manager 412. Since some communications will be server initiated, such as message receipt from devices, the client applications will have to configure their IPC channel as an IpcServerChannel as well. Use of other types of communication channels are contemplated by this disclosure.

Figure 6:
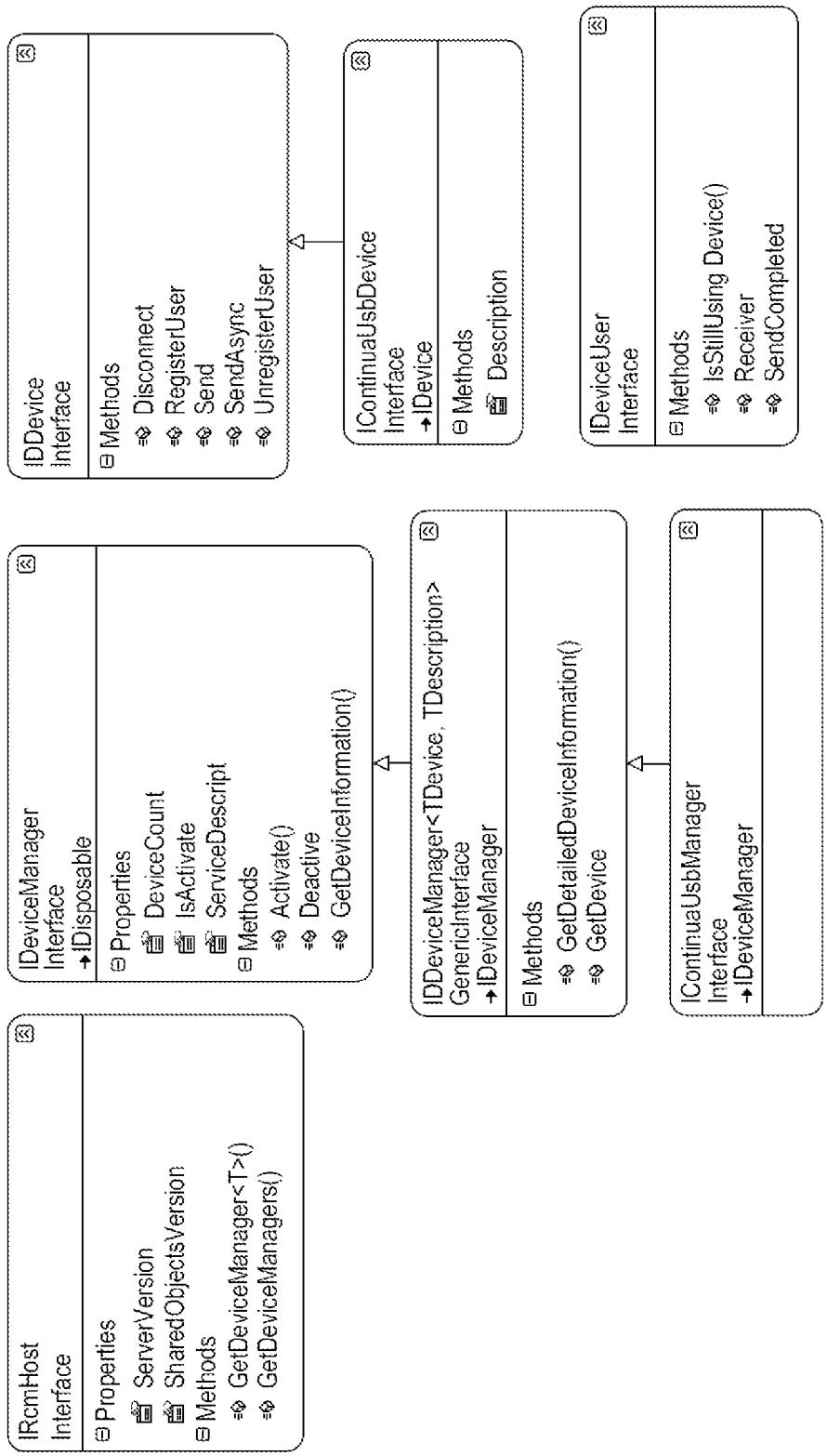
FIG. 6 is a diagram depicting the primary interfaces needed for communication between the connection manager and client applications in accordance with an exemplary embodiment.

Interfaces for all of the serializable objects that will be used for communication between the connection manager 412 and client applications are stored the SharedObjects assembly. Primary interfaces needed for communication are depicted in FIG. 6. Placing these interfaces in their own assembly ensures that there is no direct coupling between the connection manager 412 and client applications. Client applications only need to know the communication channel used by connection manager 412, and the interfaces for the shared objects.

IRcmHost is the only remotable object defined by the connection manager 412. This object serves as the main entry point for any client application. After the IPC channel has been set up, the connection manager 412 registers the RcmHost class as a remotable object. In order to begin communicating with the connection manager 412, the first thing a client application 416 must do is acquire a reference to the RcmHost object from the connection manager 412. Once the RcmHost object is acquired, methods in the host and objects returned by the host can be used just as if they were local, non-remote objects.

The connection manager 412 is preferably configured to process connections to multiple medical devices and clients simultaneously. Furthermore, the design must enable new types of medical devices to be added easily, without affecting existing functionality. To this end, the connection manager 412 primarily makes use of the manager design pattern. The manager handles issues related to accessing, creating, and destroying the device objects. A client that needs a specific device must first obtain it from the manager. Once the device has been acquired, all further interaction is done directly with the device. In order to ensure the system is easily upgradable, each type of device will require a new manager.

For each type of device supported by the connection manager 412, new device and manager interfaces must be defined. Client applications will ask for the specific device manager they are interested in using. This allows the interface for each device to be specific, appropriate, and well-defined. This also ensures that a client application only ever communicates with the specific types of devices which it supports and for which it was intended. Finally, this approach also makes it easier to add support for new features and devices without breaking backwards compatibility with the existing devices and interfaces. This is in contrast to approaches which use a single, monolithic interface for various kinds of devices. The monolithic interface can quickly become large and cumbersome as it must support the superset of features across all devices, even though a particular feature may only make sense or be supported in the context of one specific device.

Figure 7A:
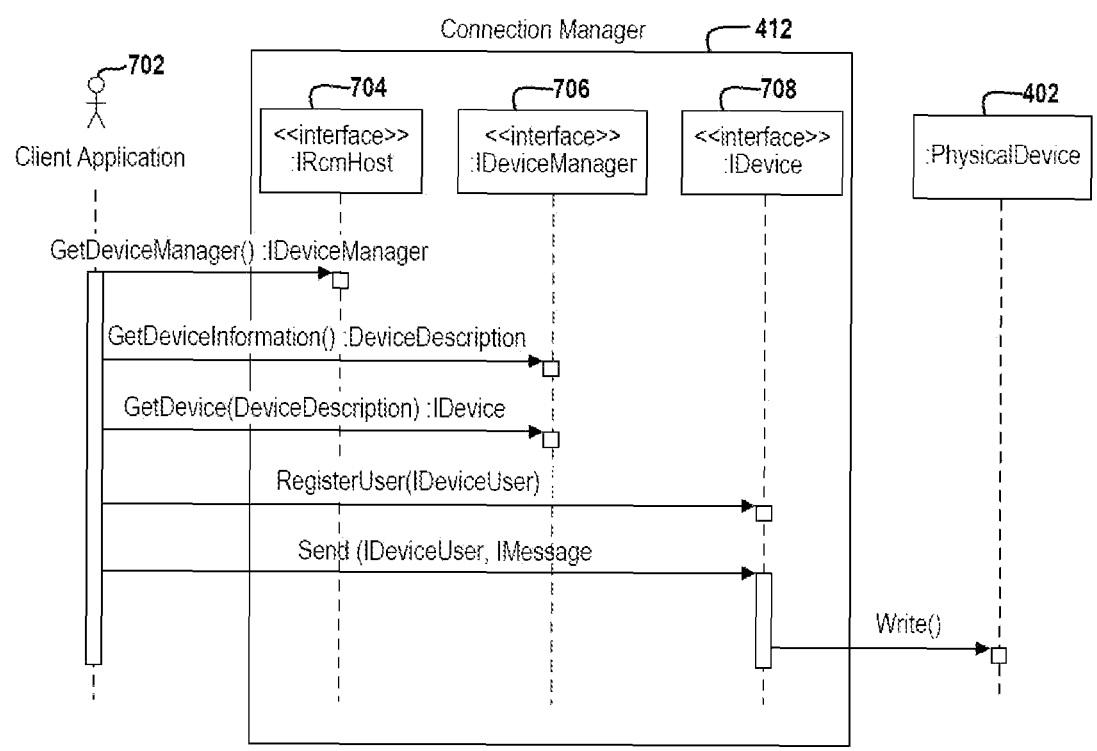
FIG. 7A is a sequence diagram illustrating the registration process of a client application in the exemplary embodiment.

Connection manager 412 supports multiple simultaneous device and client connections. However, it is imperative that only a single client at a time has access to a given device. In order to guard against multiple accesses, client applications must implement the IDeviceUser interface. The IDeviceUser interface enables a client application to register with a specific device or devices they wish to use as shown in FIG. 7A. Of note, a first client application 702 registers with the IDevice interface 706 against a particular device 402. The registered device user will have exclusive access to the device until it is unregistered.

Figure 7B:
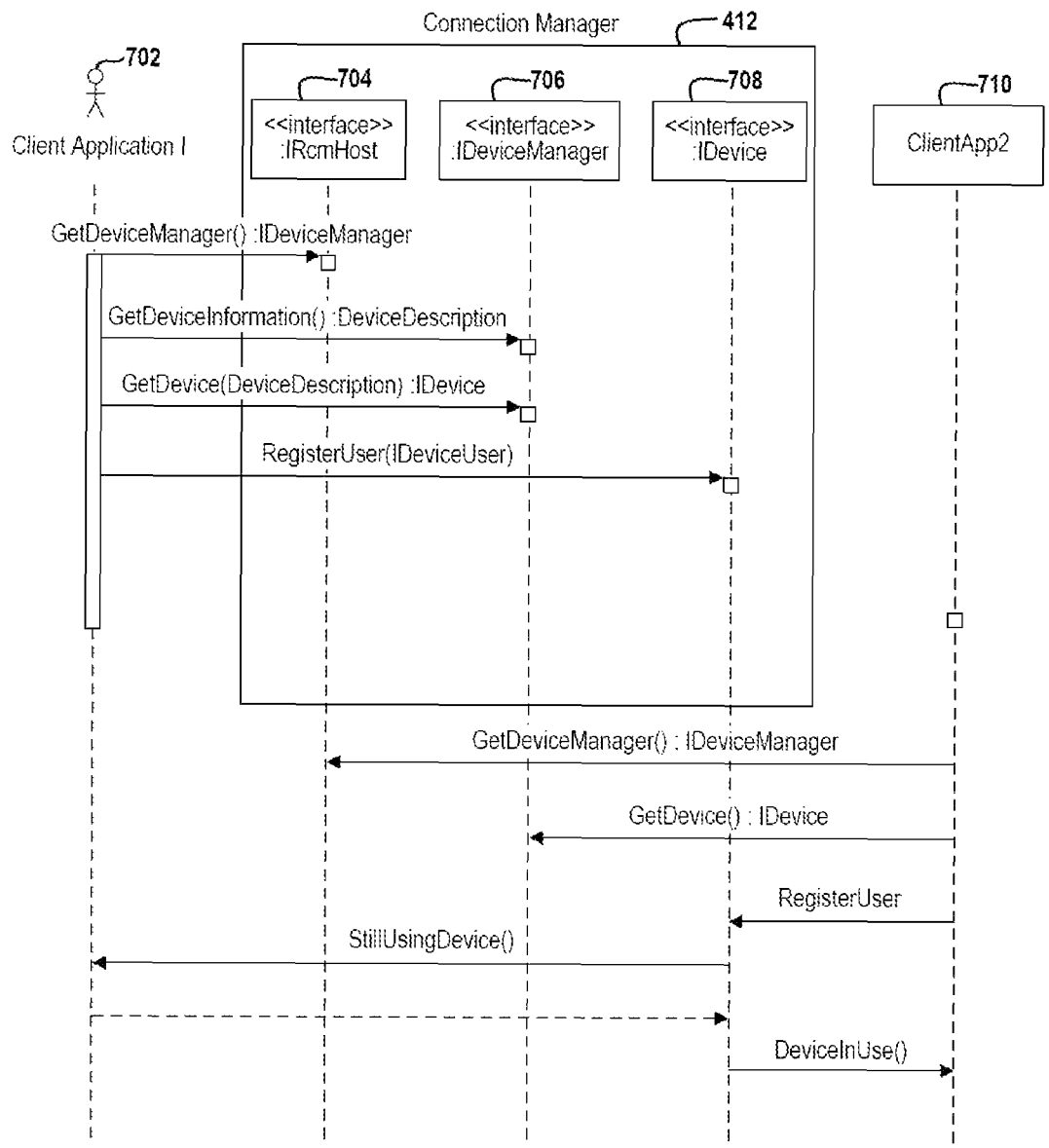
FIG. 7B is a sequence diagram illustrating the contention resolution amongst client applications in the exemplary embodiment.

In FIG. 7B, a second client application 710 tries registering against the same device. In this case, the IDevice interface 708 will check if the first client application 702 is still using the connection to the particular device. When the data connection remains in use by the first client application 702, the IDevice interface 708 will inform the second client application 710 and deny its attempt to register against the device. In this way, the IDevice interface 708 implements a first to register access rule for mitigating concurrent access requests for the data connection with the device and thus functions as the contention manager.

It is envisioned that the contention manager may be configured to implement other types of access rules. For example, the second client application 710 may be assigned a higher priority than the first client application 702. When the second client application 710 tries registering with the IDevice interface 708, priority values assigned to each client application are compared. Assuming the second client application 710 has a higher priority value than the first client application 702, the IDevice interface 708 may operate to unregister the first client application 702 in favor of registration by the second client application 710. Other types of access rules may be implemented by the contention manager.

The IDeviceUser interface also declares methods used by the devices to provide notification when a message is received, or when the sending of a message completes. This is similar in spirit to an Observer design pattern, although tailored specifically to the purpose of sending and receiving messages. Although .NET events may be used, this design specifically avoids using .NET events because they can be problematic to use in a distributed application. Since a particular client may disconnect unexpectedly, an exception could be thrown when trying to send these messages. In the case of events, this would create the need for very careful handling and manual management of the objects subscribed to every remote event.

Figure 8:
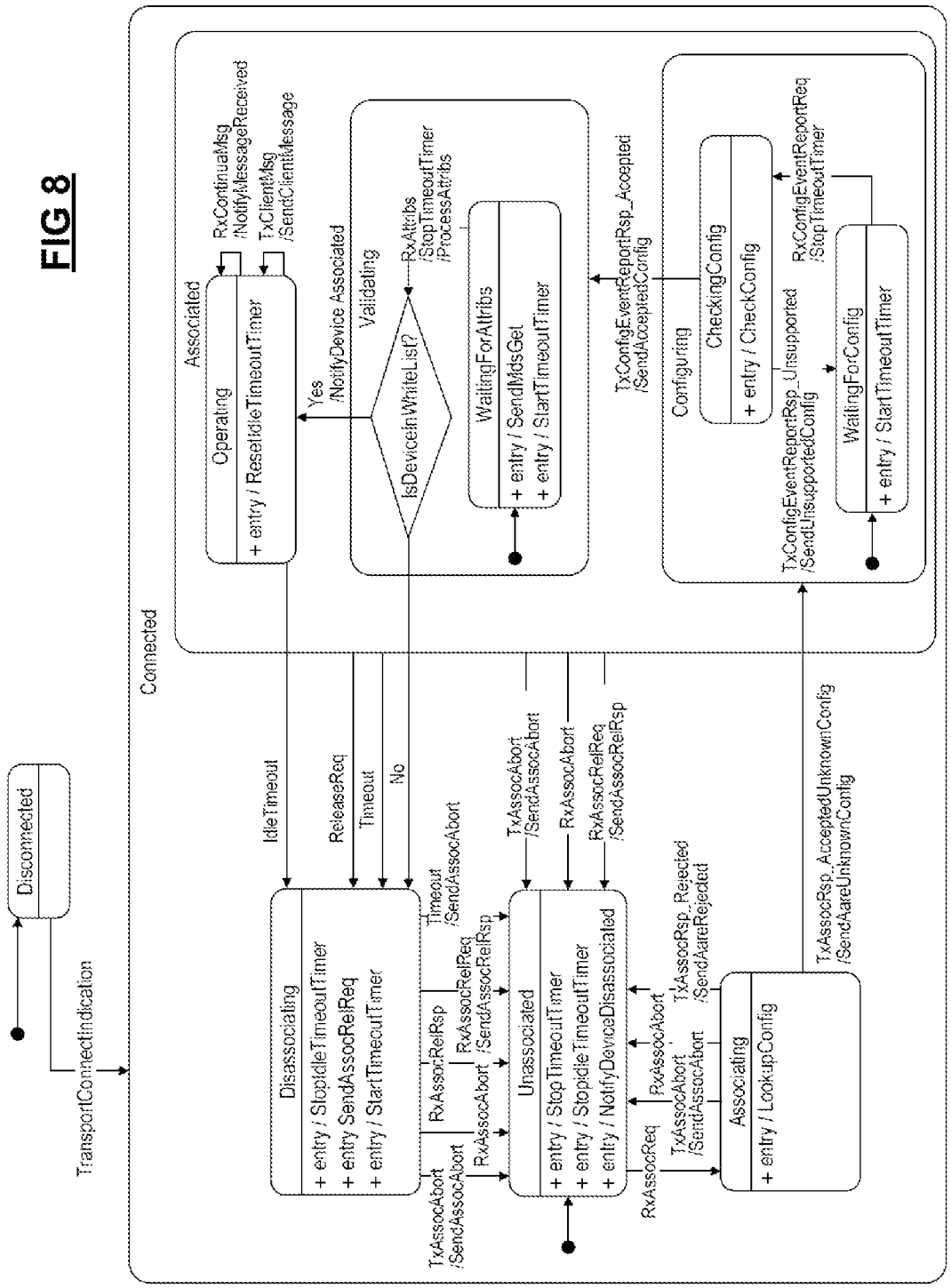
FIG. 8 is an exemplary state machine diagram for a USB device in the exemplary embodiment.

In the exemplary embodiment, the connection manager 412 supports Continua USB devices that use the Personal Healthcare Device Class (PHDC). The USB communication is provided via the RcmTransport library described below. The ContinuaUsbManager receives notification from the RcmTransport library whenever a new USB device using the PHDC interface is connected or disconnected, and manages the creation and destruction of ContinuaUsbDevice objects accordingly. An exemplary state machine for the ContinuaUsbDevice object is depicted in FIG. 8.

Figure 9:
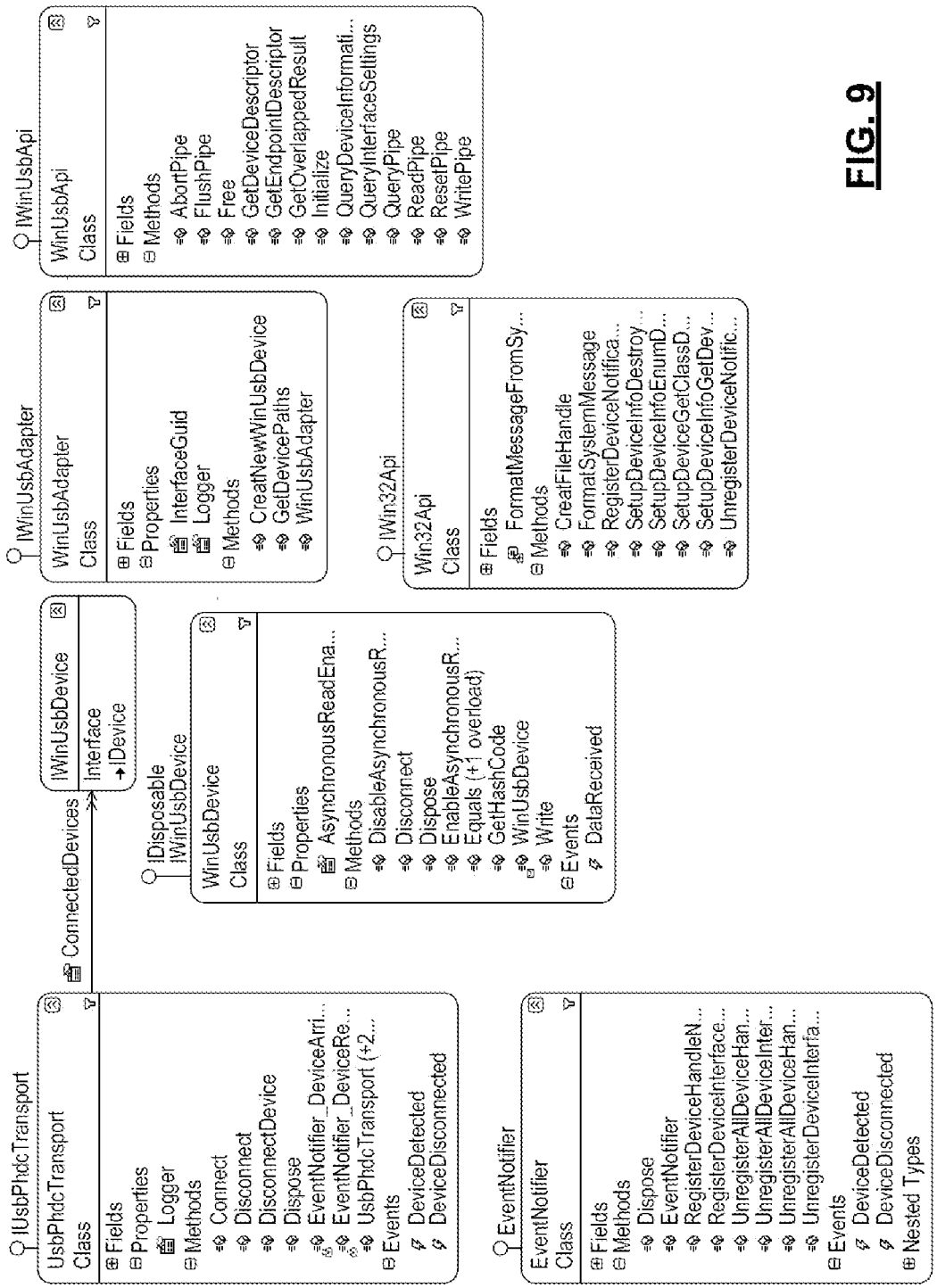
FIG. 9 is a diagram depicting classes contained in the RcmTransport assembly of the exemplary embodiment.

FIG. 9 depicts the classes contained in the RcmTransport assembly. The RcmTransport assembly contains classes which provide the actual communication with physical devices. In the exemplary embodiment, connection manager 412 supports transport for USB devices with the Personal Healthcare Device Class identifiers. These classes use the unmanaged WinUsb and Win32 libraries provided by Microsoft for communication with USB devices. Thus, the classes may include UsbPhdcTransport class, an EventNotifier class, a WinUsbDevice class, a WinUsbAdapter class, a WinUsbApi class and a Win32Api class.

In operation, the RcmTransport assembly uses a Manager design pattern, where the 'XxxTransport' class acts as the manager. The UsbPhdcTransport class uses the WinUsbAdapter class to detect connected USB PHDC devices, and create instances of WinUsbDevice. Each WinUsbDevice creates a separate thread specifically designed to wait for incoming data, and fires an event which forwards that data to where it will be processed. There is a 1-to-1 correspondence between a ContinuaUsbDevice and a WinUsbDevice as shown in FIG. 9. However, it is readily understood that the connection manager 412 may be configured to support other types of devices and thus include other suitable classes.

The above description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The term computer program, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

What is claimed is:

1. A computer-implemented diabetes management system that supports connectivity of applications residing on a medical device, comprising:
a medical device that performs a diabetes care function in relation to a patient and stores data pertaining to the function;
a diabetes care management device in data communication with the medical device and further includes:
a connection management module configured to receive an associate request from the medical device and operable to establish a data connection with the medical device in accordance with IEEE standard 11073;
a first application separate from the connection management module and residing on the diabetes care management device, wherein the first application interacts with the connection management module to communicate via the connection with the medical device, wherein the first application acquires a reference to a remotable object from the connection management module and instantiates the remotable object, such that the remotable object exposes methods which allow the first application to communicate with the connection management module; and the diabetes management system further comprises a listing of devices interoperable with the diabetes care management device and accessible to the connection management module, wherein, upon receipt of an associate request, the connection management module queries the listing of devices and establishes the data connection when the associate request is received from a medical device on the listing of devices.

2. The computer-implemented diabetes management system of claim 1 wherein the connection management module operates to disassociate from the medical device when the medical device is not on the listing of devices.

3. The computer-implemented diabetes management system of claim 1 wherein the connection management module receives a registration request from the first application for the data connection with the medical device and registers the data connection for use by the first application.

4. The computer-implemented diabetes management system of claim 3 wherein the connection management module receives messages over the data connection from the medical device and routes the messages to the first application.

5. The computer-implemented diabetes management system of claim 3 further comprises a listing of devices interoperable with the diabetes care management device and accessible to the first application, wherein the first application queries the listing of devices and establishes the data connection when the associate request is received from a medical device on the listing of devices.

6. The computer-implemented diabetes management system of claim 1 wherein the connection management module is configured to receive data over the data connection from the medical device and store the data for subsequent access by a client application in a transient data store accessible to the connection management module.

7. The computer-implemented diabetes management system of claim 1 wherein wherein the connection management module establishes an inter-process communication (IPC) channel for communication with the first application.

8. The computer-implemented diabetes management system of claim 1 wherein the connection management module communicates with the first application in accordance with the .NET framework.

9. A diabetes care management device that supports contention resolution amongst applications residing thereon, comprising:
a connection management module configured to receive an associate request from a medical device and, in response to the associate request, operate to establish a data connection with the medical device in accordance with IEEE standard 11073, wherein the connection management module includes a remotable object such that the remoteable object exposes methods which allow applications to communicate with the connection management module;
a first application separate from the connection management module and residing on the diabetes care management device, wherein the first application interacts with the connection management module to communicate via the connection with the medical device;
a second application separate from the connection management module and residing on the diabetes care management device, wherein the second application interacts with the connection management module to communicate via the connection with the medical device; and
a contention manager configured to receive a request to access the data connection from both the first and second application and operable to grant access to one of the first application or the second application in accordance with an access rule, wherein the connection management module and the contention manager are implemented as non-transitory computer-readable storage medium having stored thereon, computer-executable instructions executed by a computer processor.

10. The diabetes care management device of claim 9 wherein the contention manager operates to deny access to the other of the first application or the second application in accordance with the access rule.

11. The diabetes care management device of claim 9 wherein the connection management module receives a registration request from the first application for the data connection with the medical device and registers the data connection for use by the first application.

12. The diabetes care management device of claim 11 wherein the connection management module receives messages over the data connection from the medical device and routes the messages to the first application.

13. The diabetes care management device of claim 11 wherein the connection management module receives a registration request from the second application for the data connection with the medical device while the data connection is registered for use by the first application and denies the registration request from the second application.

14. The diabetes care management device of claim 11 wherein the connection management module receives a registration request from the second application for the data connection with the medical device while the data connection is registered for use by the first application, unregisters the data connection for use by the first application and registers the data connection for use by the second application.

15. The diabetes care management device of claim 9 wherein the connection management module establishes an inter-process communication (IPC) channel for communication with the first application.

16. The diabetes care management device of claim 15 wherein the first application operates over the IPC channel to acquire a reference to a remotable object from the connection management module and instantiates the remotable object, where the remotable object exposes methods which allow the first application to communicate with the connection management module.

* * * * *